United States Patent
Wright (10) Patent No.: US 6,479,309 B1
(45) Date of Patent: Nov. 12, 2002

(54) METHOD AND APPARATUS FOR DETERMINING PROCESS LAYER CONFORMALITY

(75) Inventor: Marilyn I. Wright, Austin, TX (US)

(73) Assignee: Advanced Micro Devices, Inc., Austin, TX (US)

(*) Notice: Subject to any disclaimer, the term of this patent is extended or adjusted under 35 U.S.C. 154(b) by 28 days.

(21) Appl. No.: 09/865,286

(22) Filed: May 25, 2001

(51) Int. Cl.⁷ .............................................. H01L 21/66
(52) U.S. Cl. .............................. 438/16; 716/4; 118/679
(58) Field of Search .............................. 438/16, 14–15, 438/17–18, 5–13, 800; 716/4; 118/663, 675, 676, 685

(56) References Cited

U.S. PATENT DOCUMENTS

| | | | | |
|---|---|---|---|---|
| 4,600,597 A | * | 7/1986 | White et al. | 427/240 |
| 5,393,624 A | | 2/1995 | Ushijima | 430/30 |
| 5,867,276 A | | 2/1999 | McNeil et al. | 356/445 |
| 5,880,838 A | | 3/1999 | Marx et al. | 356/351 |
| 6,051,348 A | | 4/2000 | Marinaro et al. | 430/30 |
| 6,245,584 B1 | | 6/2001 | Marinaro et al. | 438/14 |

OTHER PUBLICATIONS

Bishop et al., "Use of Scatterometry for resist process control," *SPIE Integrated Circuit Metrology, Inspection and Process Control*, 1673:441–452, 1992.

Hickman et al., "Use of diffracted light from latent images to improve lithography control," *SPIE Integrated Circuit Metrology, Inspection and Process Control*, 1464:245–257, 1991.

McNeil et al., "Scatterometry applied to microelectronics processing—Part 1," *Solid State Technology*, 37(3):29–56, 1993.

Miller and Mellicamp, "Development of an end–point detection procedure for the post–exposure bake process," *Integrated circuit metrology, inspection, and process control IX: 20–22, Feb., 1995, Santa Clara, California, SPIE Integrated Circuit Metrology, Inspection and Process Control*, 2439:78–88, 1995.

(List continued on next page.)

*Primary Examiner*—Craig Thompson
(74) *Attorney, Agent, or Firm*—Williams, Morgan & Amerson, P.C.

(57) ABSTRACT

A method for determining conformality of a process layer includes providing a wafer having a grating structure and a process layer formed over the grating structure; illuminating at least a portion of the process layer overlying the grating structure with a light source; measuring light reflected from the illuminated portion of the grating structure and the process layer to generate a reflection profile; and determining conformality of the process layer based on the reflection profile. A metrology tool adapted to receive a wafer having a grating structure and a process layer formed over the grating structure includes a light source, a detector, and a data processing unit. The light source is adapted to illuminate at least a portion of the process layer overlying the grating structure. The detector is adapted to measure light reflected from the illuminated portion of the grating structure and the process layer to generate a reflection profile. The data processing unit is adapted to determine conformality of the process layer based on the generated reflection profile.

66 Claims, 6 Drawing Sheets

OTHER PUBLICATIONS

Milner et al., "Latent image exposure monitor using scatterometry," *SPIE Integrated Circuit Metrology, Inspection and Process Control*, 1673:274–283, 1992.

Prins et al., "Scatterometric sensor for PEB process control," *Metrology, inspection, and process control for microlithography, X:Mar., 11–13, 1996, Santa Clara, California, SPIE Integrated Circuit Metrology, Inspection and Process Control*,2725:710–719, 1996.

Raymond et al., "Multiparameter process metrology using scatterometry," In: *Optical characterization techniques for high–performance microelectronic device manufacturing II, SPIE—The International Society for Optical Engineering*, 2638:84–93, Austin, Texas, Oct. 25–26, 1995.

Raymond et al., "Scatterometric sensor for lithography," In: *Manufacturing process control for microelectronic devices and circuits, SPIE—The International Society for Optical Engineering*, 2336:37–49, Austin, Texas, Oct. 20–21, 1994.

Sturtevant et al., "Post–exposure bake as a process–control parameter for chemically–amplified photoresist," *Metrology, inspection, and process control for microlithography, VII:Mar. 2–4, 1993, Santa Jose, California, SPIE Integrated Circuit Metrology, Inspection and Process Control*, vol. 1926, 1993.

Sturtevant et al., "Use of scatterometric latent image detector in closed loop feedback control of linewidth," *SPIE Integrated Circuit Metrology, Inspection and Process Control*, 2196:352–359, 1994.

\* cited by examiner

METHOD AND APPARATUS FOR DETERMINING PROCESS LAYER CONFORMALITY

BACKGROUND OF THE INVENTION

1. Field of the Invention

This invention relates generally to the field of semiconductor device manufacturing and, more particularly, to a method and apparatus for determining process layer conformality.

2. Description of the Related Art

Semiconductor integrated circuit devices are employed in numerous applications, including microprocessors. Generally, the performance of a semiconductor device is dependent on both the density and the speed of the devices formed therein. A common element of a semiconductor device that has a great impact on its performance is a transistor. Design features, such as gate length and channel length, are being steadily decreased in order to achieve higher package densities and to improve device performance. The rapid advance of field effect transistor design has affected a large variety of activities in the field of electronics in which the transistors are operated in a binary switching mode. In particular, complex digital circuits, such as microprocessors and the like, demand fast-switching transistors. Accordingly, the distance between the drain region and the source region of a field effect transistor, commonly referred to as the channel length or gate length dimension, has been reduced to accelerate the formation of a conductive channel between a source and a drain electrode as soon as a switching gate voltage is applied and, moreover, to reduce the electrical resistance of the channel.

A transistor structure has been created where the longitudinal dimension of the transistor, commonly referred to as the width dimension, extends up to 20 μm, whereas the distance between the drain and source regions, i.e., the channel length, may be reduced down to 0.2 μm or less. As the channel length is reduced to obtain the desired switching characteristic of the source-drain line, the length of the gate electrode is also reduced.

Transistors are formed through a series of steps. An exemplary transistor structure 100 is described in reference to FIGS. 1A and 1B. Initially, shallow trench isolation regions 105 are formed in a substrate 110 by etching trenches into the substrate 110 and, thereafter, filling the trenches with an appropriate insulating material (e.g., silicon dioxide). Next, a gate insulation layer 115 is formed over the substrate 110 between the trench isolation regions 105. This gate insulation layer 115 may be comprised of a variety of materials, but it is typically comprised of a thermally grown layer of silicon dioxide. Thereafter, a gate electrode 120 for the transistor 100 is formed by forming a layer of gate electrode material, typically polysilicon, above the gate insulation layer 115, and patterning the layer of gate electrode material using known photolithography and etching techniques to thereby define the gate electrode 120. Of course, millions of such gate electrodes 120 are being formed across the entire surface of the substrate 110 during this patterning process.

Figure 1A:
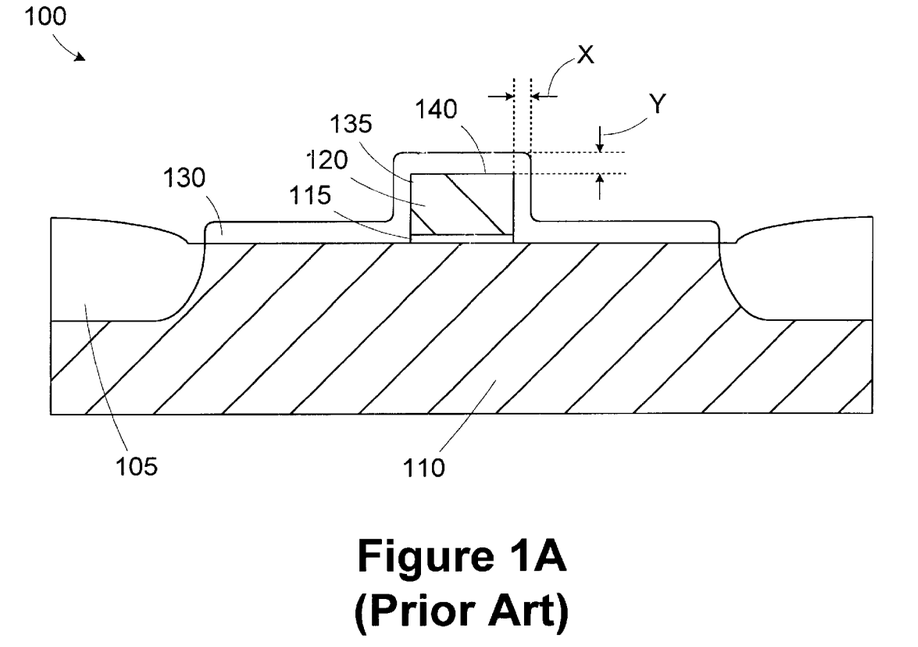
FIGS. 1A and 1B are cross sections of an exemplary semiconductor device on which a process layer is deposited over a grating structure.
Figure 1B:
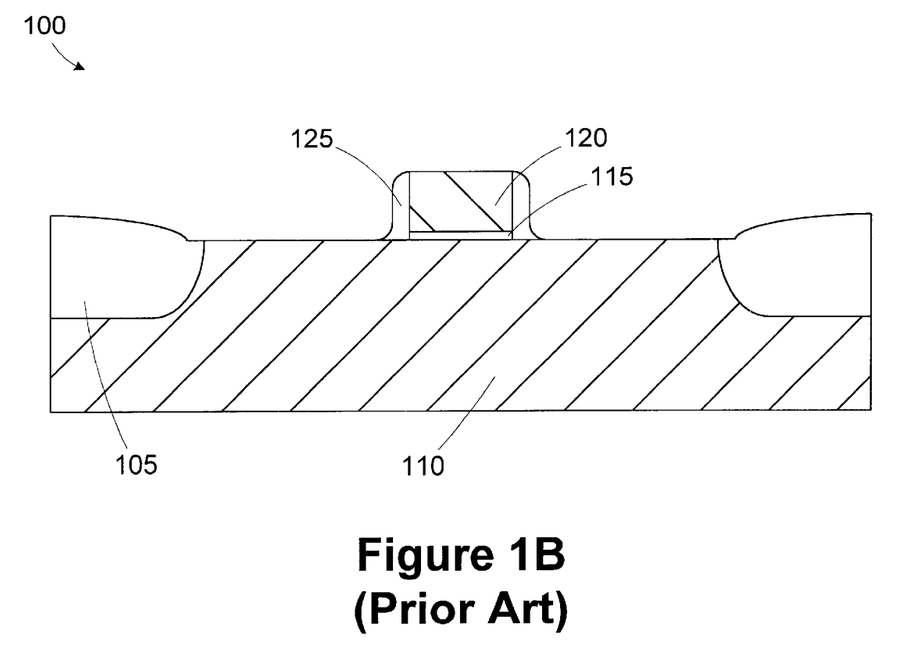

To form active regions of the transistor 100 a series of implants are performed, whereby a variety of dopant atoms may be implanted into the substrate. Typically, a halo implant is performed to reduce short channel effects arising from the small dimensions of the transistor and a lightly doped drain (LDD) or extension implant is performed is performed to reduce the junction capacitance of the transistor 100. Thereafter, a relatively high concentration of dopant atoms may be implanted into the substrate to complete the formation of the source/drain regions. This latter implant is sometimes referred to as a source/drain implant. To control the location of some of the implant regions, spacers 125 are formed about the gate electrode 120. To form the spacers 125 a layer 130 of insulating material (e.g., silicon dioxide) is formed over the substrate 110 and gate electrode 120. The insulting layer 130 is anisotropically etched until the substrate 110 is exposed, leaving a portion of the insulating layer 130 adjacent the gate electrode 120 intact to form the spacers 125. Subsequently, a second set of spacers (not shown) may be formed over the spacers 125 to define the boundaries for the source/drain implant. Typically, the second set of spacers (not shown) are formed using a layer of silicon nitride in the same manner.

The eventual width of the spacers 125 is determined, at least in part, by the thickness of the portion of the insulating layer 130 disposed over the sidewalls 135 of the gate electrode 120. The time required to complete the etch process to form the spacers 125 depends on the thickness of the portion of the insulating layer 130 disposed over the substrate 10 and top surface 140 of the gate electrode.

The conformality of a layer, such as the insulating layer 130 is defined as the ratio between the sidewall deposition thickness "X" (ie., perpendicular to the substrate 110) to the flat area deposition thickness "Y" (i.e., parallel to the substrate 110). The conformality of a deposited layer varies with respect to the particular material being deposited and the density of the underlying features. A process layer deposited over a low density topography typically exhibits a higher degree of conformality. The conformality of the layer ultimately affects the width of the spacers 125. Typically, conformality is studied during the process characterization phase, not during actual production runs of the device being manufactured. Commonly used examination techniques to determine deposited film conformality are destructive, cross-section techniques.

Normal variation in the deposition process during production runs can affect the conformality of the deposited layer. Because no in-line conformality monitoring is available, the variation propagates through the other processing steps. For example, a variation in the conformality of the insulating layer 130 can cause a variation in the width of the spacers 125 and a corresponding variation in the size and spacing of the implant regions. Variations in the implant regions can induce variations in the performance of the completed devices. Generally, increased variation reduces throughput, yield, and profitability.

The present invention is directed to overcoming, or at least reducing the effects of, one or more of the problems set forth above.

SUMMARY OF THE INVENTION

One aspect of the present invention is seen in a method for determining conformality of a process layer. The method includes providing a wafer having a grating structure and a process layer formed over the grating structure; illuminating at least a portion of the process layer overlying the grating structure with a light source; measuring light reflected from the illuminated portion of the grating structure and the process layer to generate a reflection profile; and determining conformality of the process layer based on the reflection profile.

Another aspect of the present invention is seen in a metrology tool adapted to receive a wafer having a grating structure and a process layer formed over the grating structure. The metrology tool includes a light source, a detector, and a data processing unit. The light source is adapted to illuminate at least a portion of the process layer overlying the grating structure. The detector is adapted to measure light reflected from the illuminated portion of the grating structure and the process layer to generate a reflection profile. The data processing unit is adapted to determine conformality of the process layer based on the generated reflection profile.

BRIEF DESCRIPTION OF THE DRAWINGS

The invention may be understood by reference to the following description taken in conjunction with the accompanying drawings, in which like reference numerals identify like elements, and in which.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Figure 2:
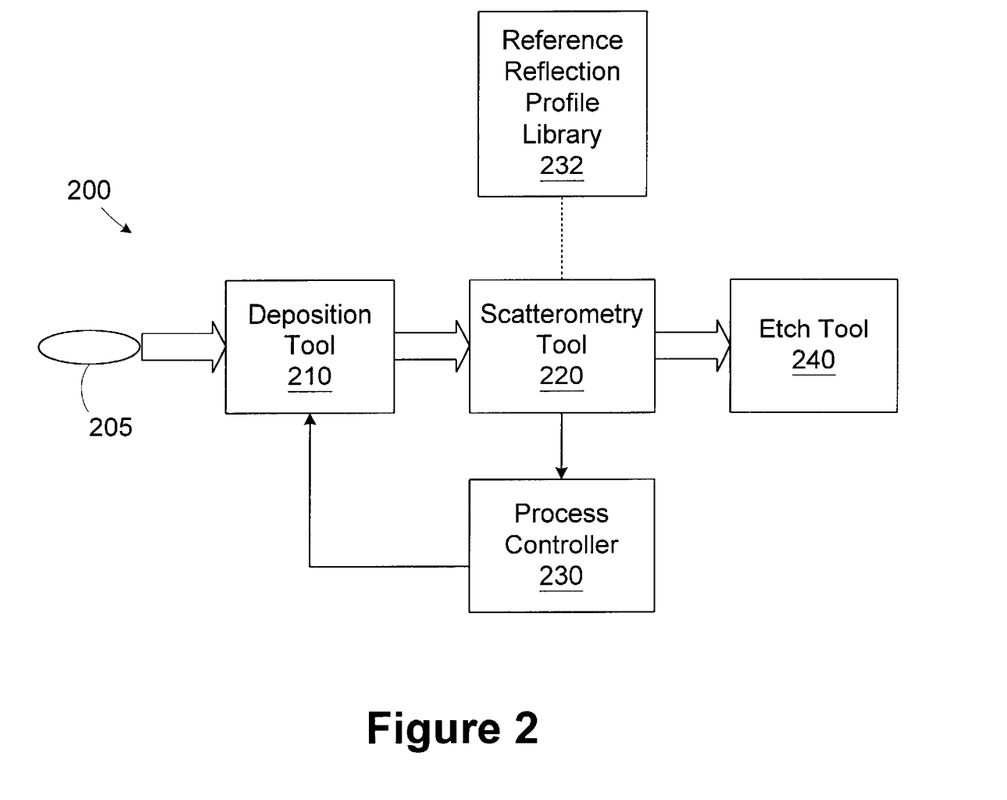
FIG. 2 is a simplified diagram of an illustrative processing line for processing wafers in accordance with one illustrative embodiment of the present invention.

Referring to FIG. 2, a simplified diagram of an illustrative processing line 200 for processing wafers 205 in accordance with one illustrative embodiment of the present invention is provided. The processing line 200 includes a deposition tool 210 for depositing a process layer on the wafer 205. In the illustrated embodiment, the process layer may be an insulting layer, (e.g., silicon dioxide or silicon nitride) that is formed over a grating structure (e.g., gate electrode). Particular techniques for depositing process layers of various composition are well known to those of ordinary skill in the art. An exemplary tool suitable for use as the deposition tool 210 is a plasma-enhanced chemical vapor deposition (PE-CVD) tool, such as a Concept 2 offered by Novellus Systems, Inc. Corporation of San Jose, Calif. Variations in the deposition operations of the deposition tool 210 and the geometry of the features formed on the wafer 205 underlying the process layer may cause variations in the conformality of the process layer as previously described.

The processing line 200 includes a scatterometry tool 220 adapted to measure conformality of the process layer formed on the wafer 205. In general, the scatterometry tool 220 includes optical hardware, such as an ellipsometer or reflectometer, and a data processing unit loaded with a scatterometry software application for processing data collected by the optical hardware. For example, the optical hardware may include a model OP5230 or OP5240 with a spectroscopic ellipsometer offered by Thermawave, Inc. of Freemont Calif. The data processing unit may comprise a profile application server manufactured by Timbre Technologies, a fully owned subsidiary of Tokyo Electron America, Inc. of Austin, Tex. and distributed by Thermawave, Inc.

The scatterometry tool 220 may be external to the deposition tool 210 or, alternatively, the scatterometry tool 220 may be installed in an in-situ arrangement. A process controller 230 is provided for controlling the operations of other tools in the processing line based on the measured conformality of the deposited process layer. The processing line also includes an etch tool 240 for performing additional processing steps on the process layer, such as a spacer etch process. An exemplary tool suitable for use as the etch tool 240 is a Rainbow etch system offered by Lam Research Corporation of Freemont, Calif.

The process controller 230 may provide feedback information to the deposition tool 210 and adjust its operating recipe to improve the conformality of the deposition process subsequently processed wafers 205. The process controller may also provide feedforward information to the etch tool 240 for controlling etch operations on the current wafer 205 being measured by the scatterometry tool 220. These feedback and feedforward control techniques will be described in greater detail below.

In the illustrated embodiment, the process controller 230 is a computer programmed with software to implement the functions described. However, as will be appreciated by those of ordinary skill in the art, a hardware controller designed to implement the particular functions may also be used. Moreover, the functions performed by the process controller 230, as described herein, may be performed by multiple controller devices distributed throughout a system. Additionally, the process controller 230 may be a stand-alone controller, it may be integrated into a tool, such as the deposition tool 210 or the scatterometry tool 220, or it may be part of a system controlling operations in an integrated circuit manufacturing facility.

Portions of the invention and corresponding detailed description are presented in terms of software, or algorithms and symbolic representations of operations on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

An exemplary software system capable of being adapted to perform the functions of the process controller 230, as described, is the Catalyst system offered by KLA-Tencor, Inc. The Catalyst system uses Semiconductor Equipment and Materials International (SEMI) Computer Integrated Manufacturing (CIM) Framework compliant system technologies and is based on the Advanced Process Control (APC) Framework. CIM (SEMI E81-0699 Provisional Specification for CIM Framework Domain Architecture) and APC (SEMI E93-0999-Provisional Specification for CIM Framework Advanced Process Control Component) specifications are publicly available from SEMI.

In one embodiment, the scatterometry tool 220 measures conformality of the process layer as found on features formed in the production devices. For example, the scatterometry tool 220 may measure the conformality of an insulating layer (e.g., silicon dioxide or silicon nitride) deposited over a gate electrode for purposes of forming an insulative spacer around the gate electrode. In some cases, the geometry of the features or the presence of underlying structures may inhibit scatterometry measurements. Accordingly, test structures having the same general configuration as features (e.g., gate electrodes) formed on the wafer 205 may be employed. The test structures may be formed in a region of the wafer 205 not normally used for forming devices (e.g., in the periphery region where identification codes are typically scribed or in the scribe lines between production die).

Figure 3:
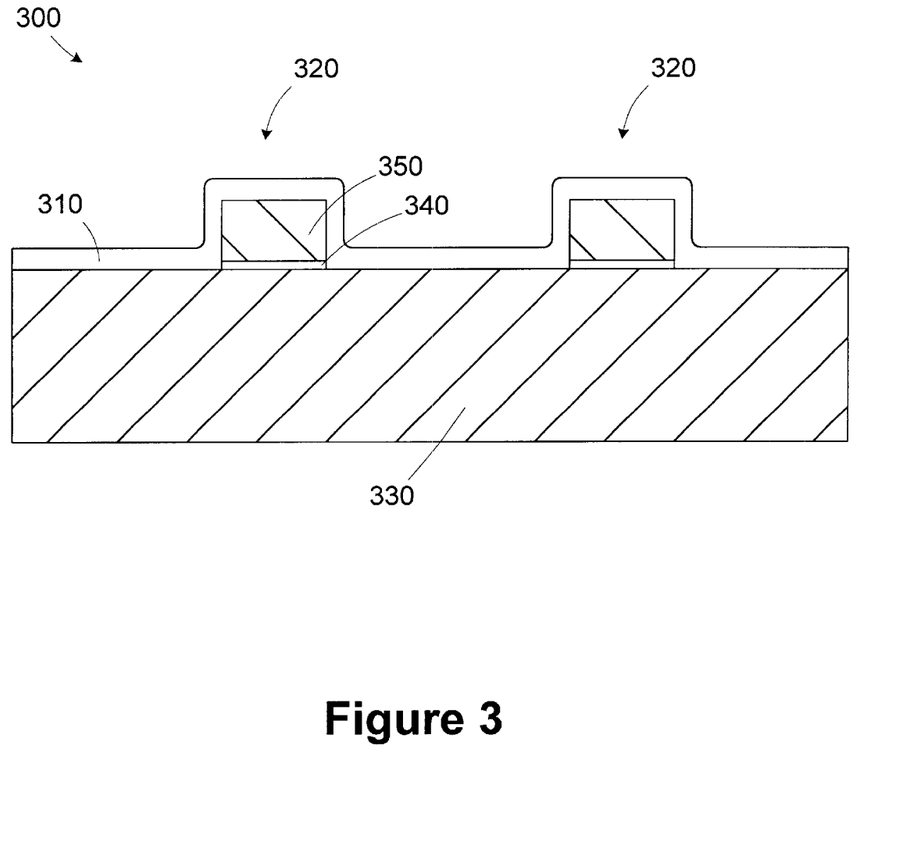
FIG. 3 is a cross section of an exemplary semiconductor device including a test grating structure for measuring the conformality of a process layer.

Referring briefly to FIG. 3, an exemplary grating structure 300 that may used as a test structure on the wafer 205 is shown. The grating structure 300 has the same general construction (e.g., geometry, materials, pitch, etc.) as features included in the production devices formed on the wafer 205. A process layer 310 is formed over the grating structure 300. In the illustrated embodiment, the grating structure 300 include stacks 320 formed on a substrate 330. The stacks 320 include a gate insulation layer 340 and a polysilicon gate electrode 350 that are formed by patterning the same process layers used to form the gate electrodes of actual transistors in the devices on the wafer 205.

Figure 4:
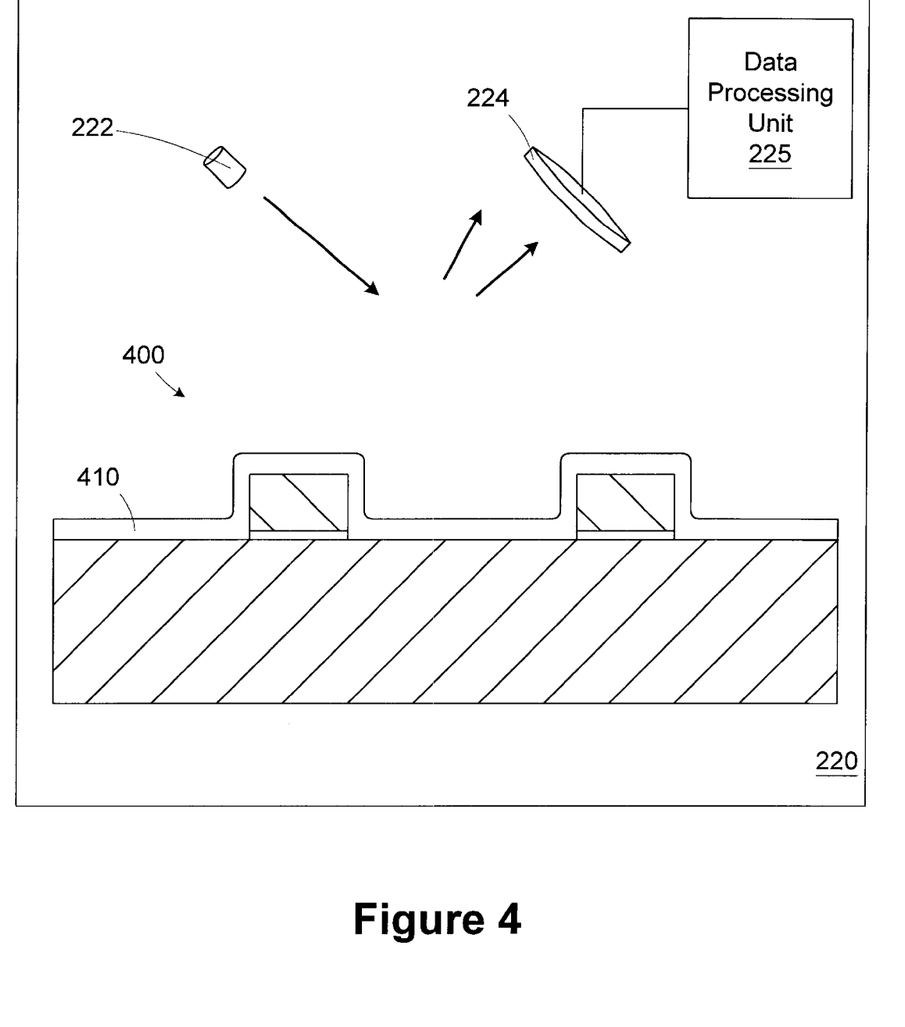
FIG. 4 is a simplified view of the scatterometry tool of FIG. 2 loaded with a wafer including a grating structure.

Turning now to FIG. 4, a simplified view of the scatterometry tool 220 loaded with a wafer 205 having a grating structure 400 and a process layer 410 overlying the grating structure is provided. The grating structure 400 may be a feature formed in a production device on the wafer 205 (i.e., STI structures are not shown in FIG. 4), or alternatively, the grating structure 400 may be a test structure similar to the grating structure 300 discussed above in reference to FIG. 3. The scatterometry tool 220, includes a light source 222 and a detector 224 positioned proximate the grating structure 400 and process layer 410. The light source 222 of the scatterometry tool 220 illuminates at least a portion of the process layer 410 overlying the grating structure 400, and the detector 224 takes optical measurements, such as intensity or phase, of the reflected light. A data processing unit 225 receives the optical measurements from the detector 224 and processes the data to determine the conformality of the process layer 300.

The scatterometry tool 220 may use monochromatic light, white light, or some other wavelength or combinations of wavelengths, depending on the specific implementation. The angle of incidence of the light may also vary, depending on the specific implementation. The light analyzed by the scatterometry tool 220 typically includes a reflected component (ie., incident angle equals reflected angle) and a refracted component (i.e., incident angle does not equal the reflected angle). For purposes of discussion here, the term "reflected" light is meant to encompass both components.

Variations in the conformality of the process layer 410 causes changes in the reflection profile (e.g., intensity vs. wavelength-tan($\delta$), phase vs. wavelength-sin($\psi$), where $\delta$ and $\psi$ are common scatterometry outputs known to those of ordinary skill in the art) measured by the scatterometry tool 220 as compared to the light scattering profile that would be present in a completely conformal process layer 410, or at least a process layer 410 having an acceptable conformality.

Figure 5A:
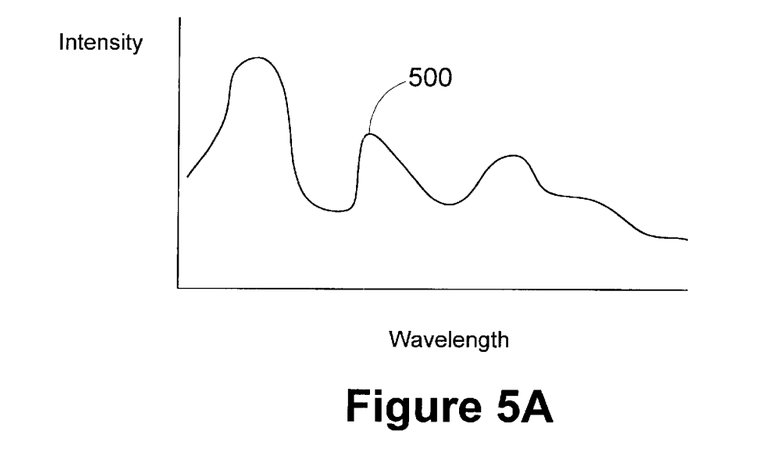
FIGS. 5A, 5B, and 5C illustrate a library of exemplary scatterometry curves used to characterize the wafer measured in the scatterometry tool of FIG. 4.
Figure 5B:
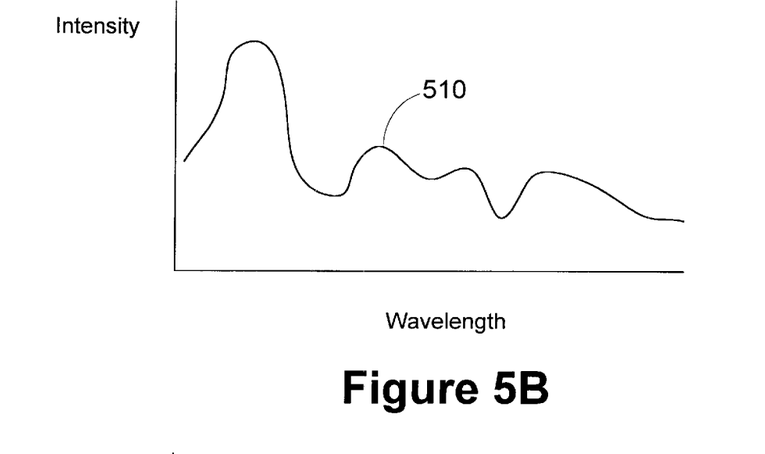
Figure 5C:
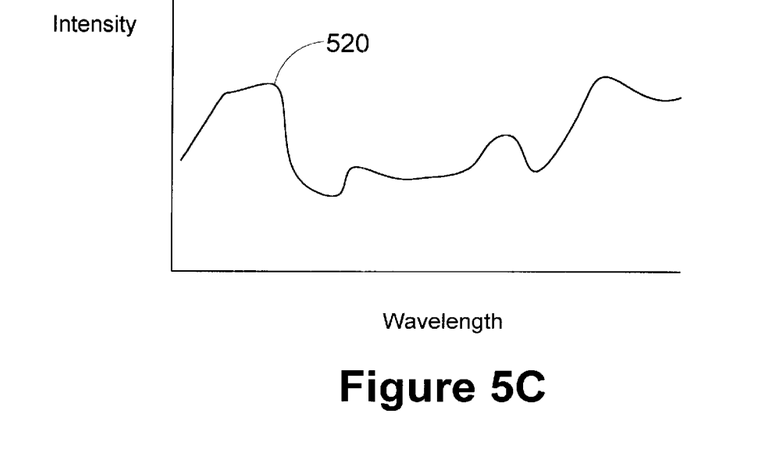

FIGS. 5A, 5B, and 5C illustrate exemplary reflection profiles 500, 510, 520 that may be included in a reference reflection profile library 232 (see FIG. 2) used by the data processing unit 225 to characterize the conformality of the process layer 410 based on the measured reflection profiles. The particular reflection profile expected for any structure depends on the specific geometry of the grating structure 400, the conformality of the process layer 410, and the parameters of the measurement technique employed by the scatterometry tool 220 (e.g., light bandwidth, angle of incidence, etc.). The profiles in the reference reflection profile library 232 are typically calculated theoretically by employing Maxwell's equations based on the characteristics of the process layer 410 and the topology and geometry of the grating structure 400. Scatterometry libraries are commercially available from Timbre Technologies, Inc. The profiles in the reference reflection profile library 232 may also be generated empirically by measuring reflection profiles of sample wafers and subsequently characterizing conformality of the measured wafers by destructive or nondestructive examination techniques.

The reflection profile 500 of FIG. 5A represents an expected profile for a process layer 410 with essentially perfect conformality (i.e., equal sidewall and flat surface thicknesses). The reflection profile 510 of FIG. 5B represents an expected profile for a process layer 410 that has a slightly reduced sidewall thickness (i.e., lower conformality), and reflection profile 520 of FIG. 5C represents an expected profile for a process layer 410 that has a significant reduction in conformality. The reflection profiles of process layers 410 with varying conformality values may be included in the reference reflection profile library 232.

The data processing unit 225 compares the measured reflection profile to the reference reflection profile library 232. Each reference profile has an associated conformality metric, which may be represented by separate sidewall and flat surface actual thicknesses or by the ratio between sidewall thickness and flat surface thickness, for example. The data processing unit 225 determines the reference reflection profile having the closest match to the measured reflection profile. Techniques for matching the measured reflection profile to the closest reference reflection profile are well known to those of ordinary skill in the art, so they are not described in greater detail herein.

In another embodiment, the process controller 230 or other external controller (not shown) may be adapted to compare the measured reflection profile to the reference reflection profile library 232. In such a case, the scatterometry tool 220 would output the matching reference reflection profile, and the process controller 230 may link that reference reflection profile to an associated conformality metric.

In another embodiment, the measured reflection profile may be compared to a target reflection profile selected from the reference reflection profile library 232 for a process layer 410 having a known and desired conformality characteristic (e.g., conformality of 1). For example, a target reflection profile may be calculated for a process layer 410 having an ideal or acceptable conformality profile using Maxwell's equations, and that target reflection profile may be stored in the reference reflection profile library 232. Thereafter, the measured reflection profile of a process layer 410 having an unknown degree of conformality is compared to the target reflection profile. Based upon this comparison, a relatively rough approximation of the conformality may be determined. That is, by comparing the measured reflection profile to the target reflection profile, conformality of the process layer 410 may be approximated, such that further matching of the measured reflection profile with additional reference reflection profiles from the reference reflection profile library 232 is unwarranted. Using this technique, an initial determination may be made as to the conformality of the process layer 410. Of course, this step may be performed in addition to the matching or correlating of a measured reflection profile to a reference reflection profile from the reference reflection profile library 232 as described above.

After receiving the conformality metric from the scatterometry tool 220, the process controller 230 may take a variety of autonomous actions. In one embodiment of the present invention, the process controller 230 is adapted to modify the operating recipe of the deposition tool 210 based on the conformality metric to control deposition operations on subsequent wafers processed by the deposition tool 210. In another embodiment of the present invention, the process controller 230 is adapted to modify the operating recipe of the etch tool 240 to control the etching of the process layer 410 based on the conformality metric. Of course, both embodiments may be combined and the process controller 230 may control the operating recipes of both the deposition tool 210 and the etch tool 240 simultaneously.

Various operating recipe parameters of the deposition tool 210 may be controlled to affect the conformality of the deposited process layer 410. For example, commonly known recipe parameters that affect conformality are the RF-bias of the plasma generator, the pressure under which the deposition process is conducted, and the time and temperature used to normalize the wafer 205 prior to deposition (i.e., commonly referred to as soak time and soak temperature).

The process controller 230 may use a control model of the deposition tool 210 for changing its operating recipe. For example, the process controller 230 may use a control model relating the measured conformality to a particular operating recipe parameter in the deposition tool 210 to control the RF bias, pressure, or soak parameters to correct for conformality deviations. The control model may be developed empirically using commonly known linear or non-linear techniques. The control model may be a relatively simple equation based model (e.g., linear, exponential, weighted average, etc.) or a more complex model, such as a neural network model, principal component analysis (PCA) model, or a projection to latent structures (PLS) model. The specific implementation of the model may vary depending on the modeling technique selected.

A conformality model may be generated by the process controller 230, or alternatively, it may be generated by a different processing resource (not shown) and stored on the process controller 230 after being developed. The conformality model may be developed using the deposition tool 210 or using a different tool (not shown) having similar operating characteristics. For purposes of illustration, it is assumed that the conformality model is generated and updated by the process controller 230 or other processing resource based on the actual performance of the deposition tool 210 as measured by the scatterometry tool 220. The conformality model may be trained based on historical data collected from numerous processing runs of the deposition tool 210.

Based on the measured conformality of the process layer 410, the process controller 230 may modify the operating recipe of the etch tool 240 to control subsequent etch processes. The width of a spacer formed around a gate electrode is determined to a large extant by the sidewall thickness of the process layer 410. However, the post-etch spacer width can also be controlled by controlling the etch time of the etch tool 240. For example, if the sidewall thickness of the process layer 410 is thicker than a desired target spacer width, the etch process can be continued for a period of time after the silicon substrate has been exposed to reduce the spacer width such that it is closer to the target spacer width. Similar to the conformality model described above for controlling the deposition tool 210, a spacer width model may be generated to control the etch time of the etch tool 240 based on the conformality measurement. The spacer etch model may be a simple, equation-based control model or a more advanced predictive model, as described above.

In another embodiment of the present invention, the process controller 230 may access previously stored metrology information regarding the profile of the underlying grating structure 400 prior to formation of the process layer 410 for use in determining the conformality of the process layer 410. For example, the profile of the grating structure 400 may have an effect on the apparent conformality. If the profile of the grating structure 400 is re-entrant, it may appear that the sidewall thickness is less than actual. Likewise, if the profile of the grating structure 400 is positive, the sidewall thickness may appear greater than actual. By factoring in the profile of the grating structure 400, the process controller 230 may correct the conformality measurement.

Figure 6:
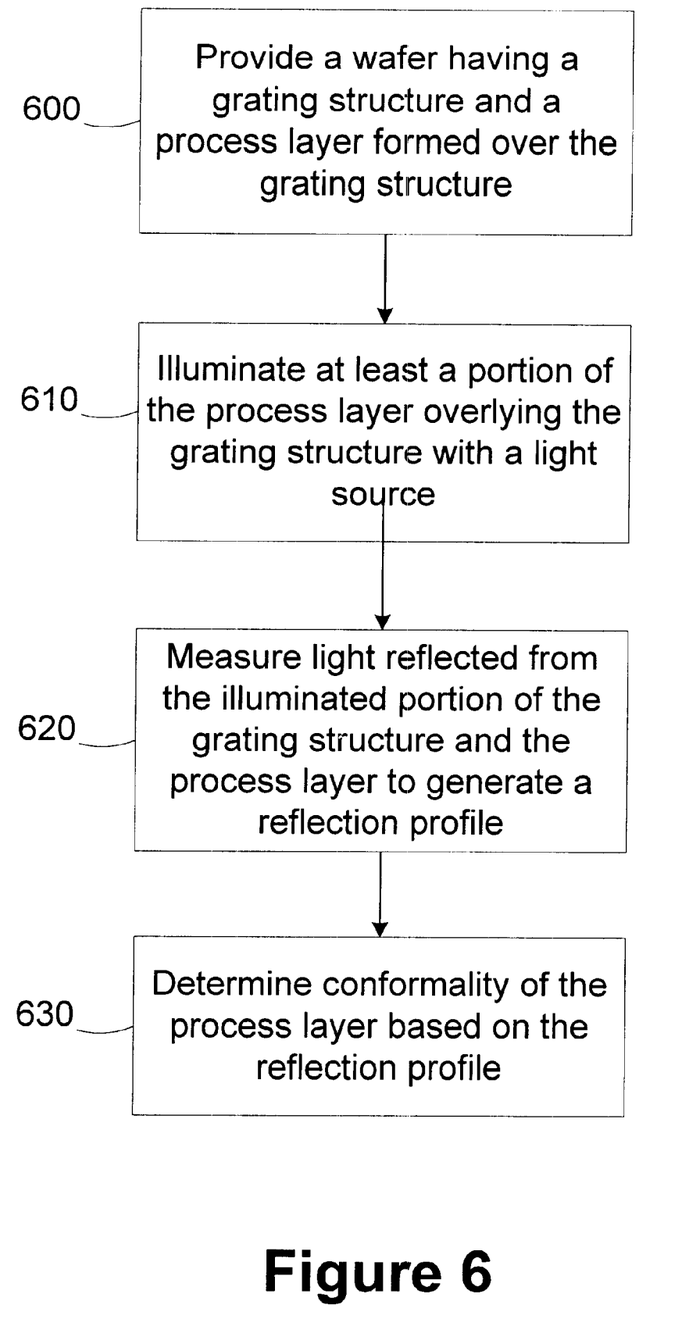
FIG. 6 is a simplified flow diagram of a method for determining conformality in a process layer in accordance with another illustrative embodiment of the present invention.

Referring now to FIG. 6, a simplified flow diagram of a method for determining conformality in a process layer in accordance with another illustrative embodiment of the present invention is provided. In block 600, a wafer having a grating structure 400 and a process layer 410 formed over the grating structure 400 is provided. In block 610, at least a portion of the process layer 410 overlying the grating structure 400 is illuminated with a light source. In block 620, light reflected from the illuminated portion of the grating structure 400 and process layer 410 is measured to generate a reflection profile. In block 630, the conformality of the process layer 410 is determined based on the reflection profile.

Monitoring conformality based on feedback from the scatterometry tool 220, as described above, has numerous advantages. The deposition tool 210 may be controlled to increase the conformality of the process layer 410. The etch tool 240 may be controlled to reduce the post etch spacer width variation. Decreased variation increases both the quality of the devices produced on the processing line 200 and the efficiency of the processing line 200.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A method for determining conformality of a process layer, comprising:
   providing a wafer having a grating structure and a process layer formed over the grating structure;
   illuminating at least a portion of the process layer overlying the grating structure with a light source;
   measuring light reflected from the illuminated portion of the grating structure and the process layer to generate a reflection profile; and
   determining conformality of the process layer based on the reflection profile.

2. The method of claim 1, wherein determining conformality of the process layer further comprises:
   comparing the generated reflection profile to a library of reference reflection profiles, each reference reflection profile having an associated conformality metric;
   selecting a reference reflection profile closest to the generated reflection profile; and
   determining conformality of the process layer based on the conformality metric associated with the selected reference reflection profile.

3. The method of claim 1, wherein generating the reflection profile comprises generating the reflection profile based on at least one of intensity and phase of the reflected light.

4. The method of claim 1, wherein providing the wafer comprises providing the wafer having the grating structure formed in a test structure on the wafer.

5. The method of claim 1, wherein providing the wafer comprises providing the afer having the grating structure formed in a production device on the wafer.

6. The method of claim 1, wherein determining conformality of the process layer further comprises:
   comparing the generated reflection profile to a target reflection profile; and
   determining conformality of the process layer based on the comparison of the generated reflection profile and the target reflection profile.

7. The method of claim 1, further comprising determining at least one parameter of an operating recipe of a processing tool based on the determined conformality.

8. The method of claim 1, wherein the grating structure includes a substrate and a stack having a sidewall disposed on the substrate, and determining the conformality further comprises determining a thickness of the process layer disposed over the sidewall.

9. The method of claim 1, wherein the grating structure includes a substrate and a stack having a sidewall disposed on the substrate, and determining the conformality further comprises determnining a ratio between a thickness of the process layer disposed over the sidewall and a thickness of the process layer disposed over the substrate.

10. A method for determining conformality of a process layer, comprising:
    providing a wafer having a grating structure and a process layer formed over the grating structure;
    illuminating at least a portion of the process layer overlying the grating structure with a light source;
    measuring light reflected from the illuminated portion of the grating structure and the process layer to generate a reflection profile;
    determining conformality of the process layer based on the reflection profile; and
    determining at least one parameter of an operating recipe of a deposition tool adapted to deposit the process layer over the grating structure based on the determined conformality.

11. The method of claim 10, wherein determining the at least one parameter of the rating recipe of the deposition tool further comprises determining at least one of an RF-bias setting, a pressure setting, a soak temperature, and a soak time based on the determined conformality.

12. The method of claim 10, wherein determining conformality of the process layer further comprises:
    comparing the generated reflection profile to a library of reference reflection profiles, each reference reflection profile having an associated conformality metric;
    selecting a reference reflection profile closest to the generated reflection profile; and
    determining conformality of the process layer based on the conformality metric associated with the selected reference reflection profile.

13. The method of claim 10, wherein generating the reflection profile comprises generating the reflection profile based on at least one of intensity and phase of the reflected light.

14. The method of claim 10, wherein providing the wafer comprises providing the wafer having the grating structure formed in a test structure on the wafer.

15. The method of claim 10, wherein providing the wafer comprises providing the wafer having the grating structure formed in a production device on the wafer.

16. The method of claim 10, wherein determining conformality of the process layer further comprises:
    comparing the generated reflection profile to a target reflection profile; and
    determining conformality of the process layer based on the comparison of the generated reflection profile and the target reflection profile.

17. The method of claim 1, wherein the grating structure includes a substrate and a stack having a sidewall disposed on the substrate, and determining the conformality further comprises determining a thickness of the process layer disposed over the sidewall.

18. The method of claim 1, wherein the grating structure includes a substrate and a stack having a sidewall disposed on the substrate, and determining the conformality further comprises determining a ratio between a thickness of the process layer disposed over the sidewall and a thickness of the process layer disposed over the substrate.

19. A method for determining conformality of a process layer, comprising:

providing a wafer having a grating structure and a process layer formed over the grating structure;

illuminating at least a portion of the process layer overlying the grating structure with a light source;

measuring light reflected from the illuminated portion of the grating structure and the process layer to generate a reflection profile;

determining conformality of the process layer based on the reflection profile; and determining at least one parameter of an operating recipe of an etch tool adapted to subsequently etch the process layer based on the determined conformality.

20. The method of claim 19, wherein determining the at least one parameter of the operating recipe of the etch tool further comprises determining an etch time based on the determined conformality.

21. The method of claim 19, wherein determining conformality of the process layer further comprises:

comparing the generated reflection profile to a library of reference reflection profiles, each reference reflection profile having an associated conformality metric;

selecting a reference reflection profile closest to the generated reflection profile; and determining conformality of the process layer based on the conformality metric associated with the selected reference reflection profile.

22. The method of claim 19, wherein generating the reflection profile comprises generating the reflection profile based on at least one of intensity and phase of the reflected light.

23. The method of claim 19, wherein providing the wafer comprises providing the wafer having the grating structure formed in a test structure on the wafer.

24. The method of claim 19, wherein providing the wafer comprises providing the wafer having the grating structure formed in a production device on the wafer.

25. The method of claim 19, wherein determining conformality of the process layer further comprises:

comparing the generated reflection profile to a target reflection profile; and determining conformality of the process layer based on the comparison of the generated reflection profile and the target reflection profile.

26. The method of claim 19, wherein the grating structure includes a substrate and a stack having a sidewall disposed on the substrate, and determining the conformnality flrter comprises determining a thickness of the process layer disposed over the sidewall.

27. The method of claim 19, wherein the grating structure includes a substrate and a stack having a sidewall disposed on the substrate, and determining the conformnality further comprises determining a ratio between a thickness of the process layer disposed over the sidewall and a thickness of the process layer disposed over the substrate.

28. A metrology tool adapted to receive a wafer having a grating structure and a process layer formed over the grating structure, comprising:

a light source adapted to illuminate at least a portion of the process layer overlying the grating structure;

a detector adapted to measure light reflected from the illuminated portion of the grating structure and the process layer to generate a reflection profile; and a data processing unit adapted to determine conformality of the process layer based on the generated reflection profile.

29. The metrology tool of claim 28, wherein the data processing unit is further adapted to compare the generated reflection profile to a library of reference reflection profiles, each reference reflection profile having an associated conformality metric, select a reference reflection profile closest to the generated reflection profile, and determine the conformality of the process layer based on the conformality metric associated with the selected reference reflection profile.

30. The metrology tool of claim 28, wherein the detector is furher adapted to generate the reflection profile based on at least one of intensity and phase of the reflected light.

31. The metrology tool of claim 28, wherein the metrology tool comprises at least one of a scatterometer, an ellipsometer, and a reflectometer.

32. The metrology tool of claim 28, wherein the grating structure comprises a test structure.

33. The metrology tool of claim 28, wherein the grating structure comprises a portion of a production device formed on the wafer.

34. The metrology tool of claim 28, wherein the data processing unit is further adapted to compare the generated reflection profile to a target reflection profile and determine conformality of the process layer based on the comparison of the generated reflection profile and the target reflection profile.

35. The metrology tool of claim 28, wherein the grating structure includes a substrate and a stack having a sidewall disposed on the substrate, and the data processing unit is further adapted to determine a thickness of the process layer disposed over the sidewall.

36. The metrology tool of claim 28, wherein the grating structure includes a substrate and a stack having a sidewall disposed on the substrate, and the data processing unit is further adapted to determine a ratio between a thickness of the process layer disposed over the sidewall and a thickness of the process layer disposed over the substrate.

37. A processing line, comprising:

a metrology tool adapted to receive a wafer having a grating structure and a process layer formed over the grating structure, the metrology tool comprising:

a light source adapted to illuminate at least a portion of the process layer overlying the grating structure;

a detector adapted to measure light reflected from the illuminated portion of the grating structure and the process layer to generate a reflection profile; and a data processing unit adapted to determine conformality of the process layer based on the generated reflection profile; and a process controller adapted to determine at least one parameter of an operating recipe of a deposition tool adapted to deposit the process layer over the grating structure based on the determined conformality.

38. The processing line of claim 37, wherein the data processing unit is fiurther adapted to compare the generated reflection profile to a library of reference reflection profiles, each reference reflection profile having an associated conformality metric, select a reference reflection profile closest to the generated reflection profile, and determine the conformality of the process layer based on the conformality metric associated with the selected reference reflection profile.

39. The processing line of claim 37, wherein the detector is flurther adapted to generate the reflection profile based on at least one of intensity and phase of the reflected light.

40. The processing line of claim 37, wherein the metrology tool comprises at least one of a scatterometer, an ellipsometer, and a reflectometer.

41. The system of claim 37 wherein the grating structure comprises a test structure.

42. The system of claim 37 wherein the grating structure comprises a portion of a production device formed on the wafer.

43. The processing line of claim 37, wherein the data processing unit is further adapted to compare the generated reflection profile to a target reflection profile and determine the conformality of the process layer based on the comparison of the generated reflection profile and the target reflection profile.

44. The processing line of claim 37, wherein the grating structure includes a substrate and a stack having a sidewall disposed on the substrate, and the data processing unit is further adapted to determine a thickness of the process layer disposed over the sidewall.

45. The method of claim 37, wherein the grating structure includes a substrate and a stack having a sidewall disposed on the substrate, and the data processing unit is further adapted to determine a ratio between a thickness of the process layer disposed over the sidewall and a thickness of the process layer disposed over the substrate.

46. The processing line of claim 37, wherein the process controller is further adapted to determine at least one of an RF-bias setting, a pressure setting, a soak temperature, and a soak time based on the determined conformality.

47. A processing line, comprising:
a metrology tool adapted to receive a wafer having a grating structure and a process layer formed over the grating structure, the metrology tool comprising:
a light source adapted to illuminate at least a portion of the process layer overlying the grating structure;
a detector adapted to measure light reflected from the illuminated portion of the grating structure and the process layer to generate a reflection profile; and
a data processing unit adapted to determine conformality of the process layer based on the generated reflection profile; and
a process controller adapted to determine at least one parameter of an operating recipe of an etch tool adapted to subsequently etch the process layer based on the determined conformality.

48. The processing line of claim 47, wherein the data processing unit is further adapted to compare the generated reflection profile to a library of reference reflection profiles, each reference reflection profile having an associated conformality metric, select a reference reflection profile closest to the generated reflection profile, and determine the conformality of the process layer based on the conformality metric associated with the selected reference reflection profile.

49. The processing line of claim 47, wherein the detector is further adapted to generate the reflection profile based on at least one of intensity and phase of the reflected light.

50. The processing line of claim 47, wherein the metrology tool comprises at least one of a scatterometer, an ellipsometer, a reflectometer, and a spectrometer.

51. The system of claim 47, wherein the grating structure comprises a test structure.

52. The system of claim 47, wherein the grating structure comprises a portion of a roduction device formed on the wafer.

53. The processing line of claim 47, wherein the data processing unit is further adapted to compare the generated reflection profile to a target reflection profile and determine the conformality of the process layer based on the comparison of the generated reflection profile and the target reflection profile.

54. The processing line of claim 47, wherein the grating structure includes a substrate and a stack having a sidewall disposed on the substrate, and the data processing unit is further adapted to determine a thickness of the process layer disposed over the sidewall.

55. The method of claim 47, wherein the grating structure includes a substrate and a stack having a sidewall disposed on the substrate, and the data processing unit is further adapted to determine a ratio between a thickness of the process layer disposed over the sidewall and a thickness of the prcess layer disposed over the substrate.

56. The processing line of claim 47, wherein the process controller is further adapted to determine an etch time based on the determined conformality.

57. A method for determining conformnality of a process layer, comprising:
providing a wafer having a grating structure and a process layer formed over the grating structure;
illuminating at least a portion of the process layer overlying the grating structure with a light source;
measuring light reflected from the illuminated portion of the grating structure and the process layer to generate a reflection profile;
comparing the generated reflection profile to a library of reference reflection profiles, each reference reflection profile having an associated conformality metric;
selecting a reference reflection profile closest to the generated reflection profile; and
determining conformality of the process layer based on the conformality metric associated with the selected reference reflection profile.

58. A method for determining conformality of a process layer, comprising:
providing a wafer having a grating structure and a process layer formed over the grating structure;
illuminating at least a portion of the process layer overlying the grating structure with a light source;
measuring light reflected from the illuminated portion of the grating structure and the process layer to generate a reflection profile;
comparing the generated reflection profile to a target reflection profile; and
determining conformality of the process layer based on the comparison of the generated reflection profile and the target reflection profile.

59. A method for determining conformality of a process layer, comprising: providing a wafer having a grating structure and a process layer formed over the grating structure;
illuminating at least a portion of the process layer overlying the grating structure with a light source;
measuring light reflected from the illuminated portion of the grating structure and the process layer to generate a reflection profile;
comparing the generated reflection profile to a library of reference reflection profiles, each reference reflection profile having an associated conformality metric;
selecting a reference reflection profile closest to the generated reflection profile;
determining conformnality of the process layer based on the conformality metric associated with the selected reference reflection profile; and determining at least one parameter of an operating recipe of a deposition tool adapted to deposit the process layer over the grating structure based on the determined conformality.

60. A method for determining conformality of a process layer, comprising:

providing a wafer having a grating structure and a process layer formed over the grating structure;

illuminating at least a portion of the process layer overlying the grating structure with a light source;

measuring light reflected from the illuminated portion of the grating structure and the process layer to generate a reflection profile;

comparing the generated reflection profile to a target reflection profile;

determining conformality of the process layer based on the comparison of the generated reflection profile and the target reflection profile; and determining at least one parameter of an operating recipe of a deposition tool adapted to deposit the process layer over the grating structure based on the determined conformality.

61. A method for determining conformality of a process layer, comprising:

providing a wafer having a grating structure and a process layer formed over the grating structure;

illuminating at least a portion of the process layer overlying the grating structure with a light source;

measuring light reflected from the illuminated portion of the grating structure and the process layer to generate a reflection profile;

comparing the generated reflection profile to a library of reference reflection profiles, each reference reflection profile having an associated conformality metric;

selecting a reference reflection profile closest to the generated reflection profile;

determining conformality of the process layer based on the conformality metric associated with the selected reference reflection profile; and determining at least one parameter of an operating recipe of an etch tool adapted to subsequently etch the process layer based on the determined conformality.

62. A method for determining conformality of a process layer, comprising:

providing a wafer having a grating structure and a process layer formed over the grating structure;

illuminating at least a portion of the process layer overlying the grating structure with a light source;

measuring light reflected from the illuminated portion of the grating structure and the process layer to generate a reflection profile;

comparing the generated reflection profile to a target reflection profile;

determining conformality of the process layer based on the comparison of the generated reflection profile and the target reflection profile; and determining at least one parameter of an operating recipe of an etch tool adapted to subsequently etch the process layer based on the determined conformality.

63. A processing line, comprising:

means for receiving a wafer having a grating structure and a process layer formed over the grating structure;

means for illuminating at least a portion of the process layer overlying the grating structure with a light source;

means for measuring light reflected from the illuminated portion of the grating structure and the process layer to generate a reflection profile; and means for determining conformality of the process layer based on the reflection profile.

64. The processing line of claim 63, further comprising means for determining at least one parameter of an operating recipe of a processing tool based on the determined conformality.

65. The processing line of claim 63, further comprising means for determining at least one parameter of an operating recipe of a deposition tool adapted to deposit the process layer over the grating structure based on the determined conformality.

66. The processing line of claim 63, further comprising means for determining at least one parameter of an operating recipe of an etch tool adapted to subsequently etch the process layer based on the determined conformality.

* * * * *

UNITED STATES PATENT AND TRADEMARK OFFICE
CERTIFICATE OF CORRECTION

PATENT NO. : 6,479,309 B1
DATED : November 12, 2002
INVENTOR(S) : Wright

It is certified that error appears in the above-identified patent and that said Letters Patent is hereby corrected as shown below:

Column 1,
Lines 20, 61 and 63, delete "system" and insert -- processing line --
Line 64, delete "roduction" and insert -- production --

Column 2,
Line 10, delete "method" and insert -- processing line --
Line 15, delete "prcess" and insert -- process --
Lines 19 and 65, delete "conformnality" and insert -- conformality --

Signed and Sealed this

Fourth Day of March, 2003

JAMES E. ROGAN
*Director of the United States Patent and Trademark Office*